(12) United States Patent
Minamino et al.

(10) Patent No.: US 9,963,728 B2
(45) Date of Patent: May 8, 2018

(54) METHOD OF MANUFACTURING FILTER AID

(75) Inventors: Atsushi Minamino, Kamakura (JP);
Hiroyuki Kurihara, Kamakura (JP);
Katsushige Yamada, Kamakura (JP);
Junpei Kishimoto, Kamakura (JP)

(73) Assignee: Toray Industries, Inc. (JP)

( * ) Notice: Subject to any disclaimer, the term of this patent is extended or adjusted under 35 U.S.C. 154(b) by 0 days. days.

(21) Appl. No.: 14/235,985

(22) PCT Filed: Jul. 27, 2012

(86) PCT No.: PCT/JP2012/069109
§ 371 (c)(1),
(2), (4) Date: Jan. 29, 2014

(87) PCT Pub. No.: WO2013/018678
PCT Pub. Date: Feb. 7, 2013

(65) Prior Publication Data
US 2014/0158642 A1   Jun. 12, 2014

(30) Foreign Application Priority Data

Jul. 29, 2011   (JP) .................... 2011-167541

(51) Int. Cl.
| | |
|---|---|
| *C12P 19/14* | (2006.01) |
| *B01J 20/24* | (2006.01) |
| *B01D 24/00* | (2006.01) |
| *B01D 24/02* | (2006.01) |
| *C08H 8/00* | (2010.01) |

(Continued)

(52) U.S. Cl.
CPC .............. *C12P 19/14* (2013.01); *B01J 20/24* (2013.01); *B01J 20/28038* (2013.01); *C08B 37/0057* (2013.01); *C08H 8/00* (2013.01); *C08L 1/02* (2013.01); *C08L 5/14* (2013.01); *C12H 1/063* (2013.01); *C12P 19/02* (2013.01);
(Continued)

(58) Field of Classification Search
CPC .................... B01J 20/28038; B01J 2220/4831
See application file for complete search history.

(56) References Cited

U.S. PATENT DOCUMENTS 4,371,552 A  *  2/1983  Posorske .................... 426/50
4,428,969 A  *  1/1984  Muller et al. .................. 426/53
(Continued)

FOREIGN PATENT DOCUMENTS

| JP | 55-075715 | 6/1980 |
|---|---|---|
| JP | 58-040145 | 3/1983 |

(Continued)

OTHER PUBLICATIONS

JP07088365 Spec Machine Translation—Apr. 4, 1995.*
(Continued)

*Primary Examiner* — Krishnan S Menon
*Assistant Examiner* — Bradley R Spies
(74) *Attorney, Agent, or Firm* — DLA Piper LLP (US)

(57) ABSTRACT

A method of producing a filter aid includes: (A) obtaining a pretreated biomass by pulverization treatment and/or thermochemical treatment of a cellulose-containing biomass; (B) treating the pretreated biomass obtained in (A) with cellulase to obtain a cellulase-treated product; and (C) obtaining a solid content of the cellulase-treated product of (B).

3 Claims, 2 Drawing Sheets

(51) Int. Cl.
*C08L 1/02* (2006.01)
*B01J 20/28* (2006.01)
*C12H 1/07* (2006.01)
*C12P 19/02* (2006.01)
*C08B 37/00* (2006.01)
*C08L 5/14* (2006.01)
*B01D 61/04* (2006.01)
*C02F 11/12* (2006.01)
*C02F 11/14* (2006.01)

(52) U.S. Cl.
CPC ....... *B01D 61/04* (2013.01); *B01J 2220/4831* (2013.01); *C02F 11/122* (2013.01); *C02F 11/14* (2013.01)

(56) References Cited

U.S. PATENT DOCUMENTS

| | | | |
|---|---|---|---|
| 6,615,991 | B1 | 9/2003 | Rettenmaier |
| 2006/0084164 | A1* | 4/2006 | Penttila et al. ............ 435/252.3 |
| 2007/0231443 | A1* | 10/2007 | Goto et al. .................... 426/594 |
| 2011/0162810 | A1* | 7/2011 | Faul ......................... D21B 1/32 162/4 |
| 2011/0250637 | A1* | 10/2011 | Kurihara .............. B01D 61/022 435/41 |

FOREIGN PATENT DOCUMENTS

| | | |
|---|---|---|
| JP | 61-038611 | 2/1986 |
| JP | 05-049924 | 3/1993 |
| JP | 07-088365 | 4/1995 |
| JP | 09-173728 | 7/1997 |
| JP | 11-323752 | 11/1999 |
| JP | 2001-55679 | 2/2001 |
| JP | 2008-150719 | 3/2008 |
| JP | 2008-535664 | 4/2008 |
| JP | 2008-161125 | 7/2008 |
| SU | 1 178 763 | 9/1985 |
| WO | WO 2010067785 A1 * | 6/2010 ........... B01D 61/022 |

OTHER PUBLICATIONS

"Pretreatment of Lignocellulosic Biomass (McMillan) excerpt.pdf" McMillan, J. D. Pretreatment of lignocellulosic biomass. In: Enzymatic Conversion of Biomass for Fuels Production; Himmel, M. E., Baker, J. O., Overend, R. P., Eds.; American Chemical Society: Washington, DC, 1994; pp. 293-300.*

"JP070-88365 Human Translation.pdf"—Iimori et al—Apr. 4, 1995.*

Extended European Search Report dated May 8, 2015 from corresponding European Patent Application No. 12 82 0010.

* cited by examiner

METHOD OF MANUFACTURING FILTER AID

TECHNICAL FIELD

This disclosure relates to a method of producing a cellulose-based filter aid.

BACKGROUND

The process of obtaining a clear liquid from a highly turbid liquid is an important process in the food industry and in drainage treatment. As a method of removing suspended substances contained in a highly turbid liquid from the liquid, centrifugation is known.

As a centrifuge to be used in the centrifugation, a screw decanter-type centrifuge is known. However, although this centrifuge is known to be excellent from the viewpoint of the processing speed and scale-up, its centrifugal force is limited to only about 2000 to 3000 G so that efficient removal of suspended components is difficult. Another example of the centrifuge is a De Laval-type centrifuge, which is a high-speed continuous centrifuge with a centrifugal force of about 8000 G. However, treatment at a high solids concentration is impossible with this centrifuge. Moreover, particulate components cannot be completely removed by this centrifuge and they partially remain, which is problematic. Still another example of the centrifuge is a Sharples-type ultra-high-speed centrifuge with a centrifugal force of about 20,000 G. This centrifuge employs batch-type discharge, and the size of the centrifuge cannot be easily increased because of limitation of the strength, which is problematic.

Another effective method of increasing clarity of a highly turbid liquid is filtration. In the food industry, drainage treatment and the like, there are methods in which a highly turbid liquid of interest is filtered using a filter aid through a suction filtration device such as a precoat filter or through a pressure filtration device such as a filter press. Known examples of such methods include those using diatomaceous earth or pearlite, especially diatomaceous earth, as a filter aid (see Derek B. Purchas, Mompei Shirato, "Solid-liquid Separation Equipment Scale-up," Gihodo Shuppan Co., Ltd. (1979)). However, it has been proposed that filter aids using diatomaceous earth may cause problems in disposal of used diatomaceous earth and safety of the diatomaceous earth itself (see Toshiro Murase/Eikichiro Aktasuka/Masato Shibata, "Solid-liquid Separation," Korin Publishing Co., Ltd. (1988)).

Filter aids using organic substances such as cellulose have been developed to solve these problems. However, in treatment of a highly turbid liquid, a cellulose-derived filter aid is less effective in increasing clarity of the filtrate than diatomaceous earth, and use of a cellulose-derived filter aid results in a lower filtration rate, which is problematic To solve these problems, a method in which the particle size distribution of a cellulose powder is controlled to use the cellulose powder as a filter aid (see JP 9-173728 A), and a method in which the content of cellulose in the filter aid is controlled (see JP 58-40145 A) have been proposed. However, in those methods, clarity of the filtrate and the filtration rate are insufficient for filtration of the highly turbid liquid, and the performances of these methods are poorer than the performance of diatomaceous earth.

Thus, to obtain a clear liquid from a highly turbid liquid, it could be helpful to provide a cellulose-based filter aid having higher performance to remove suspended substances than conventional filter aids, and a method of producing it.

SUMMARY

We discovered that a filter aid obtained by cellulase treatment of a cellulose-containing biomass can be used as a filter aid that allows efficient filtration of a liquid with low filterability.

We thus provide:

(1) A method of producing a filter aid, the method comprising the steps of: (A) obtaining a pretreated biomass by pulverization treatment and/or thermochemical treatment of a cellulose-containing biomass; (B) treating the pretreated biomass obtained in the Step (A) with cellulase to obtain a cellulase-treated product; and (C) obtaining a solid content of the cellulase-treated product of the Step (B).

(2) The method according to (1), wherein the cellulase comprises cellobiohydrolase.

(3) The method according to (1) or (2), wherein the degradation residue rate of the water-insoluble cellulase-treated product as determined by the LAP method of NREL is not less than 1.5 times higher than the rate determined before the cellulase treatment.

(4) The method according to any one of (1) to (3), wherein the thermochemical treatment is at least one selected from the group consisting of alkali treatment, ammonia treatment, acid treatment, hydrothermal treatment and steam explosion treatment.

(5) A filtration method comprising filtering a high turbidity liquid together with a filter aid obtained by the method for producing a filter aid according to any one of (1) to (4).

(6) The method according to (5), wherein the filtration method is filter press.

(7) The method according to (5) or (6), wherein the amount of dry product of the filter aid is not less than 0.5% by mass and less than 25% by mass with respect to the liquid to be filtered.

(8) A cellulose-based filter aid comprising a water-insoluble cellulase-treated product of a cellulose-containing biomass.

(9) The filter aid according to (8), wherein the cellulase comprises cellobiohydrolase.

A cellulose-based filter aid having higher performance to remove suspended substances than conventional filter aids can be obtained. With this filter aid having higher performance to remove suspended substances, a clear liquid can be obtained from a highly turbid liquid. More specifically, with our filter aid, a clear filtrate can be efficiently obtained from a liquid with low filterability, and filtration treatments that have been difficult so far such as processing of wastewater derived from a biomass and processing of microorganism-derived substances, can be realized with a filter aid derived from cellulose, which is an organic substance. Therefore, processing of a liquid can be carried out with low environmental load at low cost.

More specifically, for the purpose of obtaining a clear liquid from a highly turbid liquid, we discovered that the cellulose-based filter aid subjected to specific enzyme treatment has an extremely higher effect in removing suspended substances as compared to conventional cellulose-based filter aids. Further, our filter aid has an even higher effect in removing suspended substances than conventional diatomaceous earth filter aids. More surprisingly, we discovered that the filter aid also exhibits a largely improved processing rate of the waste liquid to be filtered, as compared to conventional cellulose-based filter aids. As a result of evaluation of clarity of the filtrate obtained by using the filter aid as filterability through a microfiltration membrane, we found that remarkable improvement of filterability can be achieved only in cases where the liquid was obtained using our filter aid.

DETAILED DESCRIPTION

Figure 1:
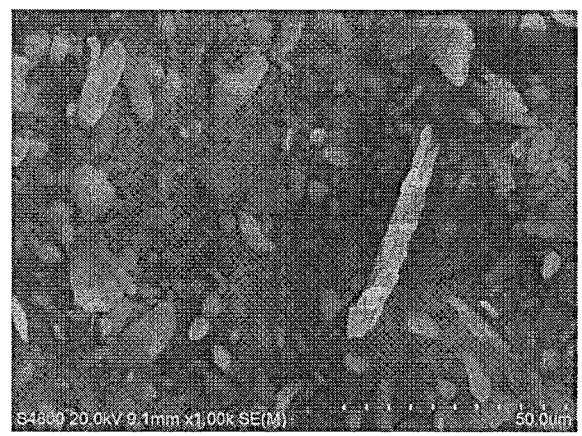
FIG. 1 is an SEM image of a cellulose-containing biomass subjected to fine pulverization treatment.

Our methods are described below in more detail.

Step (A), which is the first step of the method of producing a filter aid, is a step in which a cellulose-containing biomass is subjected to pulverization and/or thermochemical treatment to obtain a pretreated biomass.

The cellulose-containing biomass used herein means a resource derived from an organism, which resource contains cellulose at not less than 5% by mass. Specific examples of the cellulose-containing biomass include herbaceous biomasses such as bagasse (cane trash), switchgrass, napier grass, *Erianthus*, corn stover (stems and leaves of maize), residues of tubers and roots, rice straw, chaff and wheat straw; and woody biomasses such as trees and waste building materials. The content of such cellulose, excluding water, is preferably 10% to 100%, more preferably 20% to 100%.

Since such cellulose-containing biomasses contain lignin as aromatic macromolecules in addition to cellulose/hemicellulose, they are also called lignocellulose. Cellulose-containing biomasses are roughly classified into the cellulose component, hemicellulose component, lignin component and inorganic component, and the ratio of each component largely varies depending on the type of the biomass and the growth conditions.

In Step (A) of the method of producing a filter aid, a cellulose-containing biomass is subjected to pulverization and/or thermochemical treatment. In cases where both pulverization and thermochemical treatment are carried out, the order of pulverization and thermochemical treatment is not limited. These may be carried out at the same time, or pulverization and thermochemical treatment may be carried out repeatedly.

Examples of the pulverization treatment include fine pulverization treatment by mechanically cutting fibers using a cutter mill, hammer mill, grinder or the like. There are two reasons for carrying out the pulverization. First, pulverization has an effect to reduce the bulk density upon the reaction and hence to enable the reaction of as much cellulose-containing biomass as possible in the container. Second, pulverization treatment makes the reaction of thermochemical treatment or enzyme treatment easily proceed.

In the pulverization treatment, a hammer mill or cutter mill is often used, and the average particle size in such cases is 0.1 mm to 10 mm, although the average particle size is influenced by the mesh size used for classification. Examples of fine pulverization treatment include ball mill treatment, and the powder obtained can be finer than a powder obtained by pulverization treatment, due to collision among beads of ceramics such as zirconia. The average particle size is about 10 microns to 100 microns, although the average particle size is influenced by the length of time of treatment with ball mill.

The thermochemical treatment means heat treatment and/or chemical treatment of a cellulose-containing biomass. More specific examples of the pretreatment include acid treatment in which treatment is carried out with dilute sulfuric acid or a sulfite at high temperature and high pressure; alkali treatment in which treatment is carried out with an aqueous solution of an alkali such as calcium hydroxide or sodium hydroxide; ammonia treatment in which treatment is carried out with liquid ammonia or ammonia gas, or an aqueous ammonia solution; hydrothermal treatment in which treatment is carried out with pressurized hot water; and steam explosion treatment in which a cellulose-containing biomass is steamed with water vapor for a short time and the pressure is then instantaneously released to cause pulverization due to volume expansion.

Among thermochemical treatments, acid treatment is a treatment method in which an acidic aqueous solution of sulfuric acid, sulfite or the like and a cellulose-containing biomass are treated under high-temperature and high-pressure conditions to obtain a pretreated product. In general, lignin is dissolved in the acid treatment. Further, the hemicellulose component, which has low crystallinity, is first hydrolyzed, followed by degradation of the cellulose component, which has high crystallinity. By setting two or more stages of the process, selective elution of each component depending on the purpose is possible.

The acid used in the acid treatment is an acid that causes hydrolysis, and examples of the acid include citric acid, acetic acid, nitric acid and phosphoric acid. Sulfuric acid is preferred from an economic point of view. The concentration of the acid is preferably 0.1 to 15% by mass, more preferably 0.5 to 5% by mass. The reaction temperature may be 100 to 300° C. The reaction time may be 1 second to 60 minutes. The number of times of treatment may be at least one.

The liquid in the side of eluted components obtained by this thermochemical treatment comprises lignin as well as a large amount of the xylose component derived from hemicellulose, and the liquid might be applicable to production of xylose, or xylitol produced from xylose. However, since lignin is eluted similarly to hemicellulose, the lignin component is likely to cause clogging in the step of filtration treatment. Even in cases where centrifugation is attempted, efficient removal of lignin after fine pulverization is actually impossible since lignin is an aromatic organic polymer and hence has a low specific gravity. Thus, a technique that allows stable filtration is demanded to realize highly efficient removal of also such fine particle components.

Among thermochemical treatments, hydrothermal treatment is a method in which treatment is carried out with pressurized hot water at a temperature of preferably 100 to 400° C. for 1 second to 60 minutes. The treatment is usually carried out such that the cellulose-containing biomass after the treatment, which is insoluble in water at a normal temperature of 25° C., is contained at a concentration of 0.1 to 50% by mass with respect to the total weight of the cellulose-containing biomass and water. The pressure is preferably 0.01 to 10 MPa although it varies depends on the treatment temperature. In the hydrothermal treatment, the components eluted into the pressurized hot water vary depending on the temperature of the pressurized hot water. In general, as the temperature of the pressurized hot water increases, elution of tannin and lignin as the first group from the cellulose-containing biomass occurs first, and elution of hemicellulose as the second group then occurs at a temperature of not less than 140 to 150° C., further followed by elution of cellulose as the third group at a temperature higher than about 230° C. Further, at the same time as the elution, hydrolysis of hemicellulose and cellulose may occur.

The solid matter after the treatment is in the form of a powder or clay of finer wet particles produced by degradation reaction in the hydrothermal treatment, as compared to the cellulose-containing biomass before the hydrothermal treatment. By allowing the reaction to proceed under such conditions of relatively high temperature and high pressure, enzyme reaction of cellulase is likely to occur actively, and the effect of increasing the performance of the filter aid is enhanced. Further, these liquid components are useful since they contain a large amount of the xylose component derived from hemicellulose, as in the description for the acid treatment. However, these liquid components are aqueous solutions containing hemicellulose, lignin, tannin and a part of the cellulose component eluted into the pressurized hot water. Therefore, the liquid components contain lignin and the fiber component in the precipitated state, and, for example, hydrophobic colloids derived from lignin and colloids of insoluble polysaccharides, so that the turbidity is high and filtration is very difficult even by filtration treatment with a woven fabric, microfiltration membrane or the like.

Among thermochemical treatments, steam explosion treatment is a method in which vapor is blown into a cellulose-containing biomass to increase the temperature, and the biomass is exposed to the vapor at a pressure of about 1 MPa to 4 MPa for 30 seconds to 10 minutes, followed by instantaneously releasing the vapor into the atmosphere to cause pulverization. By this steam explosion treatment, the crystal state of the biomass is destroyed and lignin is decomposed by the heat at the same time, so that enzyme reaction easily occurs and hence a desired water-insoluble cellulase-treated product can be obtained. Drainage and the like are produced by idling for removing the thus obtained treated product as well as the solution component derived from the vapor and the lignin component attached to the equipment wall surface upon explosion. Further, the drainage is highly viscous, and a large amount of deposits are contained therein. Therefore, drainage treatment is difficult.

Among thermochemical treatments, alkali treatment is a treatment method in which a cellulose-containing biomass is reacted in an aqueous alkali solution, usually an aqueous solution of a hydroxide salt (excluding ammonium hydroxide). By the alkali treatment, lignin, which inhibits the reactions of cellulose/hemicellulose by cellulase, can be mainly removed. As the hydroxide salt, sodium hydroxide or calcium hydroxide is preferably used.

The concentration of the aqueous alkali solution is preferably 0.1 to 60% by mass, and treatment is carried out by adding the solution to a cellulose-containing biomass and performing the reaction at a temperature of usually 100 to 200° C., preferably 110° C. to 180° C. The treatment may be carried out one or more times. In cases where the alkali treatment is carried out two or more times, the conditions for the treatments may be different from each other. In the production of a cellulose-containing biomass by the alkali treatment, lignin is very selectively removed by the alkali so that the alkali treatment, similarly to the acid treatment, is a preferred method for production of the aid also from the viewpoints of decoloration and the like. Further, since the heating also actively causes degradation of hemicellulose, only the cellulose component can be allowed to remain in a large amount.

On the other hand, since the liquid component contains a large amount of lignin, a very turbid liquid is generated at normal temperature by suspension of precipitated components derived from lignin, and the lignin component on colloids. The resulting liquid is the so called black liquor. The black liquor is usually subjected to centrifugation and evaporation to use it as a combustion agent, but, since the black liquor is highly viscous and highly turbid, it is difficult to increase its clarity by a filtration process.

Among thermochemical treatments, ammonia treatment is a treatment method in which an aqueous ammonia solution or ammonia (liquid or gas) is reacted with a cellulose-derived biomass. Examples of the method include the methods described in JP 2008-161125 A (method using pure ammonia) and JP 2008-535664 A (method using an aqueous ammonia solution).

In the ammonia treatment, the reaction of the cellulose component with ammonia destroys the crystal state of cellulose, and isolates lignin from hemicellulose bound thereto. This reaction can be performed at a temperature lower than the temperature in other thermochemical treatments, which are carried out preferably at 40° C. to 180° C., more preferably at 60° C. to 150° C. Therefore, compared to other pretreatments, elution of the hemicellulose component from the obtained solids into the liquid-component side is less likely to occur, and hence the solids contain a large amount of hemicellulose. Therefore, as the enzyme to obtain the filter aid, an enzyme agent that is more likely to degrade hemicellulose tends to be preferably used. On the other hand, as described above, the liquid component tends to contain a smaller amount of factors that inhibit the filtration as compared to cases of other thermochemical treatments. However, since the lignin degradation reaction is caused by heat and ammonia, lignin-derived colloidal suspended components are present.

Since, as described above, the liquid component generated in the thermochemical treatment step is subjected to high temperature and high pressure, lignin present around cellulose/hemicellulose as a matrix is degraded into a colloidal state. Upon clarification of the liquid component by filtration through a woven fabric or microfiltration membrane, this lignin causes a problem that insoluble components that inhibit the clarity cannot be removed, and a problem that a membrane such as a woven fabric or microfiltration membrane is easily clogged during filtration.

In the subsequent step, Step (B), the pretreated biomass obtained in the Step (A) is treated with cellulase to obtain a cellulase-treated product.

The cellulase means an enzyme component that has an action to degrade the cellulose component in a cellulose-containing biomass, or that aids degradation of cellulose. Specific examples of the enzyme component include cellobiohydrolase, endoglucanase, exoglucanase, hemicellulase, biomass-swelling enzymes, β-glucosidase, xylanase and xylosidase. For example, since hydrolysis of the cellulose component can be efficiently carried out by a coordinate effect or complementary effect by such a plurality of enzyme components, they are preferably used. The cellulase especially preferably contains cellobiohydrolase The cellulase to be used is preferably cellulase produced by a microorganism. For example, the cellulase may comprise a plurality of enzyme components produced by a single type of microorganism, or may be a mixture of enzyme components produced by a plurality of types of microorganisms.

The microorganism that produces cellulase is a microorganism that intracellularly or extracellularly produces cellulase, preferably a microorganism that extracellularly produces cellulase. This is because the cellulase can be more easily recovered from a microorganism if the microorganism extracellularly produces cellulase.

The microorganism that produces cellulase is a microorganism that produces an enzyme component(s) described above. Since filamentous fungi classified into *Trichoderma* or *Acremonium* extracellularly produce a large amount of cellulase, they can be especially preferably used as microorganisms that produce cellulase.

The cellulase is preferably cellulase derived from a *Trichoderma* fungus. More specifically, the cellulase is more preferably cellulase derived from a *Trichoderma* fungus such as *Trichoderma reesei* QM9414, *Trichoderma reesei* QM9123, *Trichoderma reesei* Rut C-30, *Trichoderma reesei* PC3-7, *Trichoderma reesei* CL-847, *Trichoderma reesei* MCG77, *Trichoderma reesei* MCG80 or *Trichoderma viride* QM9123. The cellulase is still more preferably cellulase derived from *Trichoderma reesei*.

The cellulase may be derived from a mutant strain produced by enhancing the cellulase productivity of a *Trichoderma* filamentous fungus by mutagenesis using, for example, a mutagen or UV irradiation. For example, the cellulase may be derived from a mutant strain produced by modification of a *Trichoderma* filamentous fungus such that some enzyme components are highly expressed, which cellulase has an altered composition ratio of cellulases.

A commercially available cellulase derived from a *Trichoderma* fungus may be used. Examples of the commercially available cellulase include "Cellic CTec" (registered trademark) and "Cellic CTec2" (registered trademark), manufactured by Novozymes; "Accellerase" (registered trademark) 1000, "Accellerase" (registered trademark) 1500 and "Accellerase" (registered trademark) DUET, manufactured by Danisco Japan Ltd.; and "Cellulase from *Trichoderma reesei* ATCC 26921," "Cellulase from *Trichoderma viride*" and "Cellulase from *Trichoderma longibrachiatum*," manufactured by Sigma Aldrich.

Further, the cellulase may be used as a mixture with an enzyme derived from a fungus belonging to another genus. Examples of commercially available products of such an enzyme include "Novozymes 188", derived from *Aspergillus niger*, manufactured by Novozymes. The enzyme may also be an enzyme produced by addition of an enzyme that aids the action of cellulase.

The *Trichoderma*-derived cellulase can be obtained by culturing a *Trichoderma* fungus for an arbitrary period in a medium prepared such that the fungus produces the enzyme component. In terms of the medium component to be used, a medium supplemented with cellulose is preferably used for promoting production of cellulase. Alternatively, the culture liquid itself, or the culture supernatant after removal of *Trichoderma* cells is preferably used. Further, the medium may be supplemented with additives such as a protease inhibitor, dispersant, solubilizer and stabilizer.

In terms of the method of obtaining a cellulase-treated product, first, water is added such that the solids concentration is preferably not more than 40% by mass, more preferably not more than 20% by mass, to make the product into a slurry. Although the lower limit of the solids concentration of the product to be treated is not limited, the efficiency may be low in cases where the solids concentration is too low. Therefore, the solids concentration is usually not less than 5% by mass, preferably not less than 8% by mass. Further, it is preferred to adjust the pH to a value of 3 to 7, and to react cellulase, which is a saccharifying enzyme, at a weight ratio of $1/1000$ to $1/10$ with the cellulose-containing biomass before the thermochemical treatment and enzyme treatment in terms of the dry weight. In cases where the weight ratio of cellulase is not more than $1/1000$, the effect to cause degradation is low, while in cases where the weight ratio of cellulase is not less than $1/10$, the effect does not change, so that the weight ratio of cellulase is preferably not more than $1/10$, at which the effect reaches the upper limit, from an economic point of view. The reaction temperature is preferably 20° C. to 100° C., more preferably 30° C. to 70° C. This is because, in cases where the reaction temperature is not more than 20° C., the degradation reaction rate of enzyme is low, while in cases where the reaction temperature is not less than 100° C., deactivation of the enzyme easily occurs. The reaction time is appropriately set depending on the reaction temperature, solids concentration of the product to be treated, the activity of cellulase and the amount of cellulase used. The reaction time is usually about 6 hours to 96 hours, preferably about 12 hours to 48 hours.

In the subsequent step, Step (C), the solid content of the cellulase-treated product of Step (B) (water-insoluble cellulase-treated product) is obtained.

The solid content of the cellulase-treated product, that is, the water-insoluble cellulase-treated product, is the water-insoluble matter obtained as solids after removal, by solid-liquid separation, of the components eluted into water by the cellulase treatment in the Step (B).

The term "water-insoluble" herein means being insoluble to water, that is, a component that causes scattering of light when it is present in water. More specifically, it means a substance that precipitates by ultracentrifugation at 10000 G or, even in cases where precipitation does not occur by ultracentrifugation but the supernatant portion is in a colloidal state, the colloidal component substance is regarded as being water-insoluble.

Separation of the solid content from the cellulase-treated product can be carried out by centrifugation or filtration. The centrifugal acceleration is not limited, and, since the object can be achieved even at a low acceleration, the centrifugal acceleration is preferably about 500 G to 4000 G, more preferably about 1000 G to 3000 G, from the viewpoints of the simplicity of operation and the cost. In cases where the solid content is separated by filtration, the filtration method is not limited. Since, at this stage, the product is still highly turbid, the filtration is preferably carried out by filter press from the viewpoints of the simplicity of operation. The filter press is a filtration treatment method using a filter cloth which is a woven fabric or non-woven fabric, and can be easily carried out using a commercially available filter cloth and device. The compression pressure during the filter press is not limited, and is about 0.01 MPa to 2 MPa, preferably about 0.05 MPa to 1 MPa. The type of the filter press may be either a vertical type or a horizontal type. In terms of the method of liquid transfer, the liquid may be transferred with a pump, or may be transferred under pressure of a compressed gas. Examples of the device include "PNEUMA-PRESS" (registered trademark), manufactured by FLSmidth; "LastaFilter" (registered trademark), manufactured by Ishigaki Company, Ltd.; and "AUTOPAC" (registered trademark), manufactured by Daiki Ataka Engineering Co., Ltd.

The particle size of the water-insoluble cellulase-treated product obtained by the above-described method is not limited. This is because, based on observation of photographs, taken under the light microscope or the electron microscope, of the water-insoluble cellulase-treated product used, the product was found to be in a state where dispersed particles having various particle sizes ranging from several ten nanometers to several hundred micrometers, as well as adhesive components derived from lignin, which components could not be regarded as particles, were contained.

In terms of the composition of the water-insoluble cellulase-treated product obtained by the method, the cellulose content is preferably at 10% to 95% by mass, more preferably at 20% to 90% by mass. Many cellulose-based filter aids have a higher cellulose content and contain the cellulose component at not less than 95% by mass. However, the water-insoluble cellulase-treated product is different from those cellulose-based filter aids. Further, it is difficult to perform hydrolysis to achieve a cellulose component concentration of less than 10%, and, in such cases, the reaction time is extremely long so that the reaction is inefficient from an economic point of view.

The reason why the content cannot be increased is that, since thermochemical treatment is carried out in some cases, the lignin and hemicellulose components contained may vary. However, the compositions before and after the enzyme treatment can be defined since polysaccharide components are positively degraded by the enzyme, and the degradation residue rate (defined by the LAP method of NREL, see Reference Example 4) after the enzyme treatment is preferably not less than 1.5 times higher than that before the enzyme treatment. This is assumed to be due to the fact that the cellulose component is selectively degraded to make a part of fibrous particles into fine pieces, while only the cellulose component is degraded to increase the surface area, which results in a remarkable increase in the rate of adhesion of suspended components. The degradation residue rate is preferably not less than 1.5 times higher, more preferably 1.7 to 50 times higher. Although the degradation proceeds with time due to the reaction by cellulase, the degradation residue rate was set to preferably not less than 1.5 times based on the values observed in Examples and from an economic point of view, assuming a reaction time of 24 hours. Since the degradation reaction is an equilibrium reaction, it is difficult to achieve degradation of the whole cellulose. Therefore, the upper limit was set to preferably not more than 50 times.

We also provide a cellulose-based filter aid comprising a water-insoluble cellulase-treated product of a cellulose-containing biomass that can be produced by the above-described method. The cellulose-based filter aid herein means a filter aid prepared using as a raw material the cellulose-containing biomass described above. Examples of commercially available products of a cellulose-based filter aid include "VITACEL" (registered trademark) 600/30, 600/20, 600/10 and 600/05, "ARBOCEL" (registered trademark) 600/30, 600/20 and 600/10, "LIGNOCEL" (registered trademark), and "VIVAPUR" (registered trademark), manufactured by J. Rettenmaier & Sohne GmbH+Co. KG; "FIBRA-CEL" (registered trademark) BH40, BH100 and SW10, manufactured by Johns-Manville Corporation; "CELISH" (registered trademark) and "Pulp-flock" (registered trademark), manufactured by Daicel Finechem Ltd.; and "KC Flock" (registered trademark), manufactured by Nippon Paper Industries Co., Ltd.

The reason why the water-insoluble cellulase-treated product highly efficiently functions as a filter aid is that the product is a mixture containing particulate components produced by degradation with cellulase as well as components that hardly undergo degradation reaction by enzyme reaction even after pulverization/thermochemical treatment, and that adhesive components derived from lignin generated during the enzyme reaction adsorb suspended components. It is assumed that these effects act in a complex manner.

Examples of the use of the filter aid include service-water treatment, reclaimed-water treatment, sewage treatment, drainage treatment, chemical industry, food industry and purification of pharmaceuticals. Among these, preferred uses are sewage treatment, drainage treatment, food industry, chemical industry and pharmaceutical industry in which turbidity can be hardly decreased. A more preferred use is filtration of a turbid liquid such as the biomass-derived waste liquid generated by the pulverization treatment or thermochemical treatment described above, or a fermentation-derived waste liquid comprising a microorganism such as a yeast or bacterium.

A biomass-derived waste liquid contains a large number of hydrophobic substances derived from lignin, and a fermentation-derived waste liquid contains a large number of microorganisms such as yeasts or bacteria with sizes of several micrometers. The suspended substances in both waste liquids are organic substances having low specific gravity and high adhesiveness. These are factors likely to cause clogging of a woven fabric or microfiltration membrane during filtration treatment.

In particular, we found that the filtrate processed with the filter aid can reduce the fouling components generated upon the later membrane treatment. The filter aid is highly applicable to a pretreatment for an aftertreatment, especially a filtration process using a microfiltration membrane, ultrafiltration membrane, nanofiltration membrane, reverse osmosis membrane or the like. Further, since organic drainage derived from the liquid to be filtered is involved in the tendency to easily cause clogging of the membrane, the filter aid is especially effective in cases where the material of the membrane is derived from a macromolecular compound.

The method of filtration treatment using the filter aid is not limited, and the filtration treatment method is more preferably a method using a filter cloth which is a woven or non-woven fabric. The filter cloth may have a microfiltration-membrane-level film formed thereon. More preferably, the method is vacuum filtration or pressure filtration using the filter cloth. Examples of the vacuum filtration include the Nutsche-type, belt filter-type and belt press-type filtration methods. Examples of the pressure filtration include the centrifugal filtration-type, filter press-type and rotary press-type filtration methods. Among these, pressure filtration is preferred as the filtration method. That is, in cases where the filter aid is used, the presence of fine particles produced by enzyme treatment causes significant pressure loss due to the filter aid and, therefore, pressure filtration is preferred since it allows a large pressure difference between the primary side and the secondary side. In particular, among the pressure filtration methods, filter press can largely decrease the water content of the mixture of the used filter aid and the solid content of the treated liquid by the compression function. Since the solid content obtained by filter press can be easily burned and the combustion efficiency is high due to its low water content, secondary effects such as recovery of energy from the solid content can be obtained. The method per se of the filtration can be carried out in the same manner as in known filtration methods except that filtration is carried out together with the filter aid.

In use of the filter aid, the cellulose-containing biomass as the processed product has cellulase attached thereto. For example, by reacting SDS (sodium dodecyl sulfate) with the water-insoluble cellulase-treated product and subjecting the reaction product to SDS-PAGE analysis, whether the cellulase treatment was carried out or not can be judged. Among cellulases attached to the cellulose-containing biomass, the amount of cellobiohydrolase is especially large.

EXAMPLES

Our methods and filter aids are described below more specifically by way of Examples. However, this disclosure is not limited to the Examples below.

Each measurement value in the Examples, Comparative Examples and Reference Examples below is an average value calculated by three-point measurement.

Reference Example 1 Biomass to be Used as Sample

Rice straw and wheat straw as biomasses were pulverized using a cutter continuous mill (manufactured by IKA, MF10 basicS1) to sizes of 2 mm to 3 mm, to obtain pulverized biomasses.

Reference Example 2 Method for Measuring Water Content

The water content was measured using an infrared moisture meter (manufactured by Kett Electric Laboratory, FD-720) by keeping the sample at a temperature of 120° C. to measure the difference between the stable value after evaporation and the initial value.

Reference Example 3 Method for Measuring Turbidity

The turbidity of the liquid was measured (before filtration and after filtration) using a portable turbidimeter (manufactured by HACH, 2100P).

Reference Example 4 Method for Measuring Biomass Composition

The composition was analyzed by the following method by reference to the LAP method ("Determination of Structural Carbohydrates and Lignin in Biomass, Laboratory Analytical Procedure (LAP)") published by NREL.

An appropriate amount of the sample was subjected to measurement of the water content by the method of Reference Example 2 described above. Subsequently, the water content according to Reference Example 2 was calculated, and the obtained dry sample was subjected to intense heat at a temperature of 600° C., to determine the ash content.

The sample was transferred to a stainless steel tray, and dried in the atmosphere of the laboratory until equilibrium is almost achieved. The sample was then pulverized with a Wiley mill, and the particle size was adjusted to about 200 to 500 μm with a sieve. The sample whose conditions were controlled was dried at a temperature of 60° C. under vacuum, and the absolute-dry-mass-base content of each component was calculated by correction for the absolute dry mass. Using a balance, 0.3 g of the analysis sample was measured, and the sample was placed in a beaker. To this sample, 3 mL of 72% sulfuric acid was added, and the resulting mixture was left to stand at a temperature of 30° C. with occasional stirring for 1 hour. The resulting reaction liquid, together with 84 mL of purified water, was completely transferred to a pressure bottle, and thermolysis was carried out at a temperature of 120° C. for 1 hour in an autoclave. Thereafter, the liquid after the degradation and the residue were separated from each other by filtration, and the filtrate and washings of the residue were mixed to provide 100 mL of a test liquid. Further, a test for addition and recovery using monosaccharides for correction for over-degradation of sugars was carried out in parallel with the heat degradation. Monosaccharides (xylose, arabinose, mannose, glucose and galactose) in the test liquid were quantified by the high-performance liquid chromatographic method (GL-7400, manufactured by GL Science, fluorescence detection). Based on the monosaccharide concentrations and the amount of sample degraded in the liquid obtained after degradation, the amounts of constituent sugars in the sample were calculated.

By the addition/recovery test of monosaccharides, the amounts of constituent sugars were determined. Using the sugar overdegradation correction factor (Sf: survival factor) during the thermolysis, the amounts of constituent sugars were corrected.

Reference Example 5 Preparation of Yeast Liquid Sample

Using a yeast strain (OC2, *Saccharomyces cerevisiae*, wine yeast), a yeast liquid was prepared. In terms of the medium, the medium having the composition shown in Table 1 was subjected to filter sterilization (Millipore, Stericup 0.22 μm) before use in the fermentation.

The OC2 strain was cultured with shaking overnight in 5 mL of a fermentation medium (preculture medium) placed in a test tube (preculture). From the obtained preculture liquid, yeast was recovered by centrifugation, and the recovered yeast was washed well with 15 mL of sterile water. The washed yeast was inoculated to 100 mL of the medium shown in Table 1, and cultured with shaking for 24 hours in a 500-mL Sakaguchi flask (main culture). To obtain the thus obtained yeast liquid in a predetermined amount, the culture was performed in a plurality of flasks.

TABLE 1

| Composition | Concentration of composition |
|---|---|
| Glucose | 50 g/L |
| Drop-out MX (trade name) | 3.8 g/L |
| Yeast nitrogen base (Yeast Nitrogen Base) | 1.7 g/L |
| Ammonium sulfate | 5 g/L |

Example 1 Filter Aid Obtained by Dilute-Sulfuric-Acid Treatment/Enzyme Treatment The pulverized biomass of rice straw obtained in the Reference Example 1 was soaked in 1% aqueous sulfuric acid solution, and autoclaved at a temperature of 150° C. for 30 minutes (using an autoclave manufactured by Nitto Koatsu Co., Ltd.). Thereafter, solid-liquid separation was carried out to separate the aqueous sulfuric acid solution (hereinafter referred to as the dilute-sulfuric-acid-treated liquid) from sulfuric-acid-treated cellulose. Subsequently, the sulfuric acid-treated cellulose was mixed with the dilute-sulfuric-acid-treated liquid by stirring such that the solids concentration was 10% by mass, and the pH was adjusted to about 5 with sodium hydroxide, to obtain a mixture. To this mixture, Accellerase Duet (derived from *Trichoderma reesei*, manufactured by Danisco Japan) as a cellulase was added, and the resulting mixture was mixed by stirring at a temperature of 50° C. for 1 day to perform hydrolysis reaction, to obtain a sulfuric acid/enzyme-treated slurry. Thereafter, to simulate the conditions of a screw decanter apparatus, centrifugation (1500 G) was performed for 1 minute, to obtain a water-insoluble cellulase-treated product as solids with a water content of 76.4% by mass (hereinafter referred to as the enzyme-treated aid).

To 1 L of the dilute-sulfuric-acid-treated liquid, 500 g of the enzyme-treated aid was added to prepare a total of 1.5 kg of a mixture. After stirring the mixture to prepare a uniform slurry, filter press treatment was carried out (using a compact filtration device MO-4, manufactured by Yabuta Industries Co., Ltd.). Since the initial-stage filtrate has high turbidity, the filtrate obtained by 1 minute after the beginning of the filtration was returned to the raw liquid tank. As a filter cloth, T2731C was used, and the filtration treatment was carried out for 24 minutes. The turbidity of the dilute-sulfuric-acid-treated liquid before filter press treatment was 300 NTU, while the turbidity of the liquid after filter press treatment was 5 NTU. Using 100 mL of the dilute-sulfuric-acid-treated liquid after treatment, the operation of dead-end filtration was carried out with a microfiltration membrane ("Stericup HV" 0.45 μm (registered trademark), manufactured by Millipore). The operation of filtration was carried out at a constant suction pressure of 80 kPa. The filtration time for each condition is shown in Table 2 (differences in liquid properties evaluated using as indices turbidity of the treated liquid and the microfiltration membrane treatment (dilute-sulfuric-acid-treated liquid)).

Comparative Example 1

One hundred milliliters each of the dilute-sulfuric-acid-treated liquid of Example 1 (Liquid A), a liquid prepared by the filter press treatment without addition of the dilute-sulfuric-acid-treated liquid (Liquid B), a liquid prepared by mixing the sulfuric-acid-treated cellulose of Example 1 with the dilute-sulfuric-acid-treated liquid and subjecting the resulting mixture to the same filter press treatment as in Example 1 (Liquid C), and a liquid prepared by centrifuging the dilute-sulfuric-acid-treated liquid with a De Laval-type centrifuge (manufactured by GEA Westfalia) at 8000 G (Liquid D) was provided. The turbidity of each liquid, and the result of microfiltration membrane treatment that was carried out in the same manner as in Example 1, are summarized in Table 2. In addition to the facts shown in Example 1, we found, based on comparison with Liquid D of Comparative Example 1, that the filtration rate through the microfiltration membrane was low even in the case where the turbidity was 12 NTU and, therefore, that the turbidity and the filtration rate through the microfiltration membrane do not necessarily correlate with each other.

TABLE 2

| Liquid | Turbidity | Filtration time |
| --- | --- | --- |
| Before filter press treatment (Comparative Example 1, Liquid A) | 300 NTU | 520 seconds |

TABLE 2-continued

| Liquid | Turbidity | Filtration time |
| --- | --- | --- |
| Without addition of enzyme-treated aid; after filter press treatment (Comparative Example 1, Liquid B) | 250 NTU | 510 seconds |
| Addition of sulfuric-acid-treated cellulose; after filter press treatment (Comparative Example 1, Liquid C) | 150 NTU | 420 seconds |
| Before filter press treatment; De Laval treatment (Comparative Example 1, Liquid D) | 12 NTU | 210 seconds |
| Mixing with enzyme-treated aid; after filter press treatment (Example 1) | 5 NTU | 3 seconds |

Example 2 Filter Aid Obtained by Our Method (Using Filter Press)

The sulfuric acid/enzyme-treated slurry obtained in Example 1 was subjected to filter press treatment (compression pressure: 0.5 MPa), to obtain as solids a water-insoluble cellulase-treated product with a water content of 52.1%.

Since the obtained enzyme-treated aid did not have fluidity and was solidified, 250 g of the enzyme-treated aid crushed by hand was added to 1.8 L of the dilute-sulfuric-acid-treated liquid to prepare a total of about 2 kg of a mixture. The resulting mixture was stirred to prepare a uniform slurry, and subjected again to filter press treatment. The filtration treatment time was 30 minutes. The turbidity of this treated liquid, and the result of microfiltration membrane treatment that was carried out in the same manner as in Example 1 are shown in Table 3 (the case where an enzyme-treated aid was obtained with a filter press).

Based on a comparison with Example 1, we found that the method of solid-liquid separation before carrying out the enzyme treatment is not limited and may be either filtration or centrifugation.

TABLE 3

| Liquid | Turbidity | Filtration time |
| --- | --- | --- |
| Mixing with enzyme-treated aid; after filter press treatment (Example 2) | 3 NTU | 3 seconds |

Example 3 Filter Aid Obtained by Hydrothermal Treatment/Enzyme Treatment

Rice hulls were soaked in water, and treated with an autoclave (manufactured by Nitto Koatsu Co., Ltd.) with stirring at a temperature of 180° C. for 20 minutes. The pressure at this time was 7 MPa. Thereafter, solid liquid separation was carried out using a centrifuge (1500 G) to separate the solution component (hereinafter referred to as the hydrothermally treated liquid) and the solid component (hereinafter referred to as the hydrothermally treated biomass) from each other. To the obtained hydrothermally treated biomass component, water was added such that the solid content was 10% by mass, and an aqueous sodium hydroxide solution was added to the resulting mixture to pH 5, to prepare a slurry, followed by addition of 1/40 volume of Accellerase Duet to the slurry. Subsequently, the resulting mixture was allowed to react at a constant temperature of 50° C. with stirring for 24 hours. Thereafter, the slurry was centrifuged at a pressure of 1500 G for 1 minute to obtain a water-insoluble cellulase-treated product. The water content of the obtained enzyme-treated aid was 78.1%.

To 1 L of the hydrothermally treated liquid, 500 g of the enzyme-treated aid was added to prepare a total of 1.5 kg of a mixture, and the mixture was then stirred to provide a uniform slurry, followed by carrying out the filter press treatment in the same manner as in Example 1. The turbidity of the hydrothermally treated liquid before the filter press treatment was not less than 1000 NTU, while the turbidity of the liquid after the filter press treatment was 5 NTU. Using 100 mL of the hydrothermally treated liquid after treatment, dead-end filtration treatment was carried out with a microfiltration membrane in the same manner as in Example 1. The results are shown in Table 4 (the result obtained by carrying out microfiltration membrane treatment (hydrothermally treated liquid)). From the result of the comparison with Comparative Example 2, we found, similarly to Example 1, that, also in the case where rice hull was used and hydrothermal treatment was carried out as the thermochemical treatment such that pretreatment by the hydrothermal treatment was followed by use of the enzyme-treated filter aid, the turbidity of the treated liquid was lower and the effect of removal of suspended components was higher than in other cases. Further, we found that the filtration rate through the microfiltration membrane was remarkably improved.

Comparative Example 2

The hydrothermally treated liquid of Example 3 (Liquid E), a liquid prepared by directly subjecting the hydrothermally treated liquid to filter press treatment (Liquid F) and a liquid prepared by adding the hydrothermally treated biomass and then carrying out filter press treatment (Liquid G) were subjected to the same dead-end filtration test treatment with a microfiltration membrane as in Example 3. The results are shown in Table 4. When the hydrothermally treated liquid was directly subjected to filter press treatment, clogging of the filter cloth occurred 5 minutes later. Treated liquid could be hardly obtained, and the amount of liquid obtained was only 120 mL. One hundred milliliters of the liquid obtained was subjected as Liquid F to the same microfiltration membrane treatment.

TABLE 4

| Liquid | Turbidity | Filtration time |
| --- | --- | --- |
| Before filter press treatment (Comparative Example 2, Liquid E) | Not less than 1000 NTU | Not less than 600 seconds |
| Without addition of enzyme-treated aid; after filter press treatment (Comparative Example 2, Liquid F) | 800 NTU | Not less than 600 seconds |
| After addition of hydrothermally treated biomass; filter press treatment (Comparative Example 2, Liquid G) | 600 NTU | 540 seconds |
| Addition of enzyme-treated aid; after filter press treatment (Example 3) | 5 NTU | 3 seconds |

Example 4 Filter Aid Obtained by Steam Explosion Treatment

To a steam explosion apparatus (manufactured by Nihon Dennetsu Co., Ltd.; size, 30 L), pulverized biomass of rice straw was fed, and vapor was injected. A pressure of 2.5 MPa was kept for 2.5 minutes to perform explosion treatment. During the operation, drainage (idling drainage) was generated. The water content of the explosion-treated biomass was 84.4%. Water was added to the explosion-treated biomass such that the solid content was 10% by mass, and an aqueous sodium hydroxide solution was added to the resulting mixture to pH 5, to prepare a slurry, followed by addition of 1/40 volume of Accellerase Duet to the slurry. Subsequently, the resulting mixture was allowed to react at a constant temperature of 50° C. with stirring for 24 hours. The slurry after the reaction was subjected to filter press treatment, to obtain a water-insoluble cellulase-treated product with a water content of 50.9%.

Since the obtained enzyme-treated aid did not have fluidity and was solidified, 100 g of the enzyme-treated aid crushed by hand was added to 1.8 L of the explosion drainage to prepare a total of about 2 kg of a mixture. The resulting mixture was stirred to prepare a uniform slurry, and subjected again to filter press treatment in the same manner as in Example 1. The filtration treatment time was 20 minutes. The turbidity of the explosion drainage before the filter press treatment was not less than 1000 NTU, while the turbidity of the liquid after the filter press treatment was 2 NTU. Using 100 mL of the explosion drainage after the treatment, microfiltration membrane treatment was carried out in the same manner as in Example 1. The results are shown in Table 5 (result of microfiltration membrane treatment (explosion drainage)). Based on comparison with Comparative Example 3, we found, similarly to Example 1, that, also in the case where explosion treatment was carried out such that the explosion treatment as a physicochemical treatment was followed by use of the enzyme-treated filter aid, the turbidity of the treated liquid was lower and the effect of removal of suspended components was higher than in other cases. Further, it was found that the filtration rate through the microfiltration membrane was remarkably improved.

Comparative Example 3

Each of the explosion drainage (Liquid H), a liquid prepared by subjecting the explosion drainage to filter press treatment without addition of the aid (Liquid I), and a liquid prepared by directly adding the explosion-treated biomass and then carrying out filter press treatment (Liquid J), was subjected to the same turbidity and microfiltration treatment tests as in Example 4. The results are shown in Table 5. Liquid J, which is the liquid prepared by adding the explosion-treated biomass followed by performing filter press treatment, could be hardly processed by filter press, and clogging of the filter cloth occurred about 3 minutes after the beginning of the treatment. The amount of liquid that could be obtained was only 200 mL. From the obtained liquid, 100 mL was subjected to microfiltration membrane treatment.

TABLE 5

| Liquid | Turbidity | Filtration time |
| --- | --- | --- |
| Before filter press treatment (Comparative Example 3, Liquid H) | Not less than 1000 NTU | Not less than 600 seconds |
| Without addition of enzyme-treated aid; after filter press treatment (Comparative Example 3, Liquid I) | 650 NTU | 480 seconds |
| After addition of explosion-treated biomass; filter press treatment (Comparative Example 3, Liquid J) | 300 NTU | 240 seconds |
| Addition of enzyme-treated aid; after filter press treatment (Example 4) | 5 NTU | 3 seconds |

Example 5 Filter Aid Obtained by Alkali Treatment/Enzyme Treatment

Pulverized biomass of wheat straw was soaked in 5% aqueous sodium hydroxide solution, and autoclaved at a temperature of 150° C. for 10 minutes (using an autoclave manufactured by Nitto Koatsu Co., Ltd.). Thereafter, solid-liquid separation was carried out to separate the drainage after the sodium hydroxide treatment (hereinafter referred to as the alkali-treated liquid) and alkali-treated cellulose from each other. Subsequently, the alkali-treated cellulose was mixed with the alkali-treated liquid by stirring such that the solids concentration was 10% by mass, and the pH was adjusted to about 5 with dilute sulfuric acid, to obtain a mixture. To this mixture, Accellerase Duet was added as cellulase, and the resulting mixture was mixed by stirring at a temperature of 50° C. for 1 day to perform hydrolysis reaction, to obtain an enzyme-treated slurry. Thereafter, for simulating the conditions of a screw decanter apparatus, centrifugation (1500 G) was performed for 1 minute, to obtain a water-insoluble cellulase-treated product as solids with a water content of 77.5%.

To 1 L of the alkali-treated liquid, 500 g of the enzyme-treated aid was added to prepare a total of 1.5 kg of a mixture. After stirring the mixture to prepare a uniform slurry, filter press treatment was carried out in the same manner as in Example 1. The turbidity of the hydrothermally treated liquid before filter press treatment was 630 NTU, while the turbidity of the liquid after filter press treatment was 6 NTU. Using 100 mL of the hydrothermally treated liquid after treatment, dead-end filtration treatment was carried out with a microfiltration membrane in the same manner as in Example 1. The results are shown in Table 6 (differences in liquid properties evaluated using as indices turbidity of the treated liquid and the microfiltration membrane treatment (alkali-treated liquid)).

Comparative Example 4

Each of the alkali-treated liquid (Liquid K), a liquid prepared by subjecting the alkali drainage to the filter press treatment without addition of an aid (Liquid L), and a liquid prepared by directly adding the alkali-treated cellulose, followed by the filter press treatment (Liquid M), was subjected to the same turbidity and microfiltration treatment tests as in Example 5. The results are shown in Table 6. Based on comparison with Example 5, we found, similarly to Example 1, that, in the case where wheat straw was used as the raw material and alkali treatment was carried out as the physicochemical treatment, followed by use of the enzyme-treated filter aid, the turbidity of the treated liquid was lower and the effect of removal of suspended components was higher than in other cases. Further, we found that the filtration rate through the microfiltration membrane was remarkably improved.

TABLE 6

| Liquid | Turbidity | Filtration time |
| --- | --- | --- |
| Before filter press treatment (Comparative Example 4, Liquid K) | 630 NTU | 360 seconds |
| Without addition of enzyme-treated aid; after filter press treatment (Comparative Example 4, Liquid L) | 490 NTU | 320 seconds |
| Addition of alkali-treated cellulose; after filter press treatment (Comparative Example 4, Liquid M) | 200 NTU | 270 seconds |
| Mixing with enzyme-treated aid; after filter press treatment (Example 5) | 6 NTU | 3 seconds |

Example 6 Filter Aid Obtained by Aqueous Ammonia Treatment/Enzyme Treatment

In 2.7 kg of 1.5 N aqueous ammonia solution, 300 g of pulverized biomass of rice straw was soaked, and autoclave treatment was carried out at a temperature of 180° C. for 20 minutes (using an autoclave manufactured by Nitto Koatsu Co., Ltd.). Thereafter, solid-liquid separation was carried out to separate the drainage after the aqueous ammonia treatment (hereinafter referred to as the ammonia-treated liquid) and ammonia-treated cellulose from each other. Subsequently, the ammonia-treated cellulose was mixed with the ammonia-treated liquid by stirring such that the solids concentration was 10% by mass, and the pH was adjusted to about 5 with dilute sulfuric acid, to obtain a mixture. To this mixture, Accellerase Duet was added as cellulase, and the resulting mixture was mixed by stirring at a temperature of 50° C. for 1 day to perform hydrolysis reaction, to obtain an enzyme-treated slurry. Thereafter, to simulate the conditions of a screw decanter apparatus, centrifugation (1500 G) was performed for 1 minute, to obtain a water-insoluble cellulase-treated product as solids with a water content of 76.4%.

To 1 L of the hydrothermally treated liquid, 500 g of the enzyme-treated aid was added to prepare a total of 1.5 kg of a mixture. After stirring the mixture to prepare a uniform slurry, filter press treatment was carried out in the same manner as in Example 1. The turbidity of the hydrothermally treated liquid before the filter press treatment was 360 NTU, while the turbidity of the liquid after the filter press treatment was 3 NTU. Using 100 mL of the hydrothermally treated liquid after treatment, dead-end filtration treatment was carried out with a microfiltration membrane in the same manner as in Example 1. The results are shown in Table 7 (differences in liquid properties evaluated using as indices turbidity of the treated liquid and the microfiltration membrane treatment (ammonia-treated liquid).

Comparative Example 5

Each of the ammonia-treated liquid (Liquid N), a liquid prepared by subjecting the ammonia-treated liquid to the filter press treatment without addition of the aid (Liquid O), and a liquid prepared by directly adding the ammonia-treated cellulose and then carrying out filter press treatment (Liquid P), was subjected to the same turbidity and microfiltration treatment tests as in Example 6. The results are shown in Table 7.

Based on comparison with Example 6, we found, similarly to Example 1, that, in the case where ammonia treatment was carried out as a physicochemical treatment followed by use of the enzyme-treated filter aid, the turbidity of the treated liquid was lower and the effect of removal of suspended components was higher than in other cases. Further, we found that the filtration rate through the microfiltration membrane was also remarkably improved.

TABLE 7

| Liquid | Turbidity | Filtration time |
| --- | --- | --- |
| Before filter press treatment (Comparative Example 5, Liquid N) | 510 NTU | 300 seconds |
| Without addition of enzyme-treated aid; after filter press treatment (Comparative Example 5, Liquid O) | 420 NTU | 270 seconds |
| Addition of ammonia-treated cellulose; after filter press treatment (Comparative Example 5, Liquid P) | 180 NTU | 240 seconds |
| Mixing with enzyme-treated aid; after filter press treatment (Example 6) | 3 NTU | 3 seconds |

Comparative Example 6 Use of Diatomaceous Earth-Based Filter Aid

Using two kinds of diatomaceous earth ("Radiolite" (registered trademark) #300, manufactured by Showa Chemical Industry Co., Ltd.), the dilute-sulfuric-acid-treated liquid of Example 1, the hydrothermally treated liquid of Example 3, and a liquid prepared by removal of suspended components from the yeast liquid of Reference Example 5, were provided. First, to 1 L of each liquid, 50 g of Radiolite "#300" was added, and the resulting mixture was subjected to filter press treatment. Further, these liquids were subjected to microfiltration membrane treatment in the same manner as in Example 1. The results on the turbidity after filter press treatment and the filtration time upon the microfiltration membrane treatment are shown in Table 8 (the effect of the diatomaceous earth filter aid on various suspensions).

Based on comparison with Example 1, Example 3 and the like, we found that the filter aid obtained is more excellent than diatomaceous earth filter aids, which are conventional filter aids, in view of the effect of removal of suspended components and the filtration rate of the treated liquid through a microfiltration membrane.

TABLE 8

| Liquid to be treated | Turbidity | Filtration time |
| --- | --- | --- |
| Dilute-sulfuric-acid-treated liquid | 180 NTU | 300 seconds |
| Hydrothermally treated liquid | 750 NTU | Not less than 600 seconds |
| Yeast liquid | 80 NTU | 120 seconds |

Comparative Example 7 Filtration Using Commercially Available Cellulose-Based Filter Aids (Dilute-Sulfuric-Acid-Treated Liquid/Hydrothermal C5 Liquid/Yeast Liquid)

Each of KC Flock (manufactured by Nippon Paper Industries Co., Ltd.) and "ARBOCEL" (registered trademark) (manufactured by Rettenmaier), which are commercially available cellulose-based filter aids, was added to the dilute-sulfuric-acid-treated liquid, hydrothermally treated liquid and yeast liquid such that the dry solids concentration was 5%, and filtration treatment by filter press was carried out. Further, these liquids were subjected to microfiltration membrane treatment in the same manner as in Example 1. The results on the turbidity after filter press treatment and the filtration time upon the microfiltration membrane treatment are shown in Table 9 (the effect of KC flock on each suspension) and Table 10 (the effect of ARBOCEL on each suspension).

TABLE 9

| Liquid to be treated | Turbidity | Filtration time |
| --- | --- | --- |
| Dilute-sulfuric-acid-treated liquid | 240 NTU | 480 seconds |
| Hydrothermally treated liquid | Not less than 1000 NTU | Not less than 600 seconds |
| Yeast liquid | 240 NTU | 300 seconds |

TABLE 10

| Liquid to be treated | Turbidity | Filtration time |
| --- | --- | --- |
| Dilute-sulfuric-acid-treated liquid | 210 NTU | 450 seconds |
| Hydrothermally treated liquid | Not less than 1000 NTU | Not less than 600 seconds |
| Yeast liquid | 200 NTU | 240 seconds |

Example 7 Filter Aids Obtained by Enzyme Treatment of Commercially Available Filter Aids Using KC Flock (manufactured by Nippon Paper Industries Co., Ltd.) and "ARBOCEL" (registered trademark) (manufactured by Rettenmaier), enzymatic treatment was carried out with Accellerase DUET in the same manner as in Example 1. Each enzyme-treated product was added to the dilute-sulfuric-acid-treated liquid, hydrothermally treated liquid and yeast liquid such that the dry solids concentration was 5%, and filtration treatment by filter press was carried out. Further, these liquids were subjected to microfiltration membrane treatment in the same manner as in Example 1. The results on the turbidity after filter press treatment and the filtration time upon the microfiltration membrane treatment are shown in Table 11 (the effect of KC flock after the enzyme treatment on various suspensions) and Table 12 (the effect of ARBOCEL on various suspensions). Thus, it is suggested that, as compared to Comparative Example 7, the enzyme treatment of the commercially available cellulose filter aids with cellulase improved the performance of the filter material to remove suspended components.

TABLE 11

| Liquid to be treated | Turbidity | Filtration time |
| --- | --- | --- |
| Dilute-sulfuric-acid-treated liquid | 2 NTU | 3 seconds |
| Hydrothermally treated liquid | 6 NTU | 3 seconds |
| Yeast liquid | 2 NTU | 3 seconds |

TABLE 12

| Liquid to be treated | Turbidity | Filtration time |
| --- | --- | --- |
| Dilute-sulfuric-acid-treated liquid | 2 NTU | 3 seconds |
| Hydrothermally treated liquid | 5 NTU | 3 seconds |
| Yeast liquid | 2 NTU | 3 seconds |

Comparative Example 8 Use of Fine Pulverized Biomass (Only Fine Pulverization)

Using a planetary ball mill "PLANET H" (manufactured by GOKIN PLANETARING Inc.), fine pulverization treatment was carried out. After placing 30 g of pulverized rice straw biomass and 30 g of zirconia beads ("TORAYCERAM" (registered trademark), manufactured by Toray Industries, Inc.; particle size, 0.05 mm diameter) in a container, fine pulverization treatment was carried out for 20 hours. The resulting product was sieved through a 30-μm sieve to remove the zirconia beads, to obtain pulverized cellulose. This pulverized biomass was used as the filter aid. When the pulverized cellulose before use was observed with SEM (manufactured by Hitachi High-Technologies Corporation, S-4800), most pulverized cellulose had nonfibrous shapes with particle size of about 20 μm as shown in FIG. 1.

The results on the turbidity after filter press treatment and the filtration time upon the microfiltration membrane treatment are shown in Table 13. Based on comparison with Comparative Example 7 (Table 9, Table 10), it can be seen that the pulverized cellulose has an improved filtration performance as compared to the commercially available cellulose filter aids. This is consistent with the description in JP 9-173728 A.

TABLE 13

| Liquid to be treated | Turbidity | Filtration time |
|---|---|---|
| Dilute-sulfuric-acid-treated liquid | 60 NTU | 210 seconds |
| Hydrothermally treated liquid | 120 NTU | 300 seconds |
| Yeast liquid | 30 NTU | 120 seconds |

Example 8 Obtaining Filter Aid Obtained by Our Method (Fine Pulverization+Enzyme-Treated/Hydrothermally Treated Liquid, Yeast Liquid)

The pulverized biomass obtained in Comparative Example 8 was subjected to enzyme treatment with Accellerase DUET in the same manner as in Example 1. The resulting enzyme-treated product was added to each of the dilute-sulfuric-acid-treated liquid, hydrothermally treated liquid and yeast liquid such that the dry solids concentration was 5%, and filtration treatment by filter press was carried out. Further, these liquids were subjected to microfiltration membrane treatment in the same manner as in Example 1. The results on the turbidity after filter press treatment and the filtration time upon the microfiltration membrane treatment are shown in Table 14 (the effect of the pulverized biomass after enzyme treatment on various suspensions). Thus, it is suggested that, as compared to Comparative Example 8 (Table 13), the enzyme treatment with cellulase of the pulverized cellulose having higher filtration performance than the commercially available cellulose filter aids also remarkably improved the performance of the filter material to remove suspended components.

TABLE 14

| Liquid to be treated | Turbidity | Filtration time |
|---|---|---|
| Dilute-sulfuric-acid-treated liquid | 2 NTU | 3 seconds |
| Hydrothermally treated liquid | 4 NTU | 3 seconds |
| Yeast liquid | 2 NTU | 3 seconds |

Example 9 Use of Belt Filter (Precoat/Body Feed) (Inferior to Filter Press)

Using a vacuum horizontal belt filter (ADPEC, manufactured by Daiki Ataka Engineering Co., Ltd.), an attempt was made to obtain a clear liquid by vacuum filtration. In terms of filter materials, an enzyme-treated product of the sulfuric acid-treated cellulose was added to the dilute-sulfuric-acid-treated liquid; an enzyme-treated product of the hydrothermally treated biomass was added to the hydrothermally treated liquid; and an enzyme-treated product of the explosion-treated biomass was added to the yeast liquid; such that the solids concentration was 5% by mass. Filtration treatment with the belt filter was carried out. The results are shown in Table 15 (the effect of addition of each filter aid on various suspensions). As shown in Table 15, we found that, although vacuum filtration using the belt filter was inferior to pressure filtration using the filter press in view of the filtration rate, the belt filter showed effectiveness from the viewpoints of turbidity of the filtrate obtained and the processing speed through the microfiltration membrane.

Comparative Example 9

A similar experiment for filtration treatment using a vacuum horizontal belt filter was performed with filter materials prepared by addition of the sulfuric acid-treated cellulose to the dilute-sulfuric-acid-treated liquid; addition of the hydrothermally treated biomass to the hydrothermally treated liquid; or addition of the explosion-treated biomass to the yeast liquid; such that the solids concentration was 5% by mass. The results are shown in Table 15. Based on comparison with Example 9, it was found that use of the biomass without enzyme treatment as a filter aid has only a low effect as a filter aid.

TABLE 15

| Liquid to be treated | Method for treating filter aid | Filtration time (belt) | Turbidity (filtrate) | Filtration time (filtrate) |
|---|---|---|---|---|
| Dilute-sulfuric-acid-treated liquid (Comparative Example 9) | Sulfuric acid treatment | 1 minutes | 220 NTU | 300 seconds |
| Dilute-sulfuric-acid-treated liquid (Example 9) | Sulfuric acid treatment followed by Enzyme treatment | 20 minutes | 75 NTU | 20 seconds |
| Hydrothermally treated liquid (Comparative Example 9) | Hydrothermal treatment | 5 minutes | 750 NTU | Not less than 600 seconds |
| Hydrothermally treated liquid (Example 9) | Hydrothermal treatment followed by enzyme treatment | Not less than 30 minutes | 30 NTU | 30 seconds |
| Yeast liquid (Comparative Example 9) | Explosion treatment | 10 minutes | 50 NTU | 80 seconds |
| Yeast liquid (Example 9) | Explosion treatment followed by enzyme treatment | Not less than 30 minutes | 20 NTU | 25 seconds |

Comparative Example 10 Reaction with Hemicellulase

To the sulfuric-acid-treated cellulose obtained in Example 1, water was added, and the pH was adjusted to 6. Thereafter, the resultant was reacted with a hemicellulase, Optimase CX (manufactured by Danisco Japan Ltd.) at a temperature of 60° C. for 2 hours, followed by centrifugation to obtain solids. The thus obtained hemicellulase-treated product as a filter aid was added to the aqueous dilute sulfuric acid solution, and the resulting mixture was stirred to obtain a uniform slurry, followed by carrying out filter press treatment. The filtration treatment time was 90 minutes. The turbidity of this treated liquid and the result of microfiltration treatment carried out in the same manner as in Example 1 are shown in Table 16 (the case where hemicellulase treatment was carried out).

From the above results, we found that when hemicellulase is allowed to react, degradation occurred mostly in hemicellulose, and therefore the effect was low without treatment with cellulase for degradation of cellulose, which constitutes a large part of the cellulose-containing biomass. That is, for production of our filter aid, hemicellulase may be contained, but treatment with cellulase is indispensable. JP 2001-55679 A describes a method for bleaching lignocellulose, but it was found that this method does not allow exertion of the filtration performance of our filter aid.

TABLE 16

| Liquid | Turbidity | Filtration time |
|---|---|---|
| Addition of sulfuric-acid-treated cellulose; after filter press treatment (Comparative Example 1, Liquid C) | 120 NTU | 300 seconds |

Reference Example 6 Method of Confirming Water-Insoluble Cellulase-Treated Product In terms of confirmation of whether or not a product is the water-insoluble cellulase-treated product (enzyme-treated aid) described above, a method of analyzing enzyme attached to the water-insoluble cellulase-treated product (enzyme-treated aid) is described below.

That is, the water-insoluble cellulase-treated product is suspended in a surfactant, SDS (aqueous sodium dodecyl sulfate solution), and the resulting suspension is centrifuged at a pressure of 8000 G for 5 minutes to cause precipitation of the water-insoluble cellulase-treated product, thereby recovering the supernatant.

Figure 2:
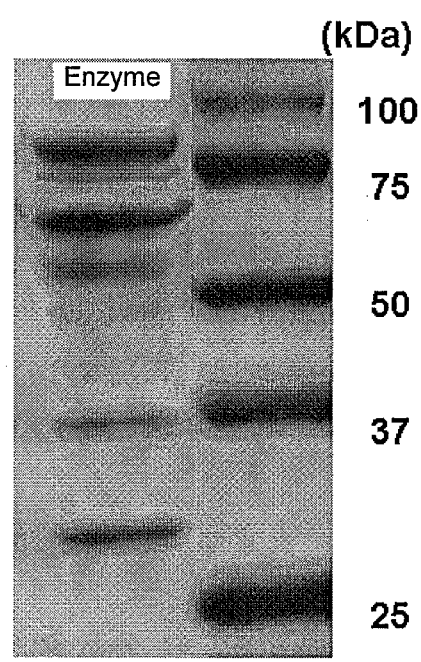
FIG. 2 is a picture showing the result of SDS-PAGE of ellulose (Accellerase DUET)
Figure 3:
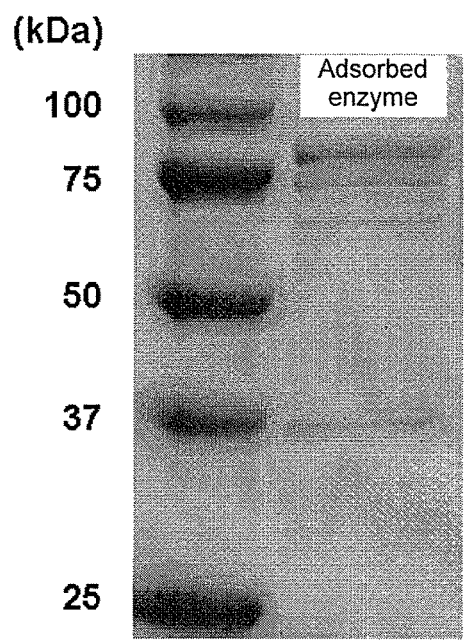
FIG. 3 is a picture showing the result of SDS-PAGE of adsorbed enzyme of a water-insoluble ellulose-treated product.

With the obtained supernatant, the same amount of a sample treatment buffer (ATTO EzApply) was mixed, and treatment was carried out at a temperature of 100° C. for 10 minutes, to obtain a treated sample. The obtained treated sample in an amount of 5 μL was applied to 15% by mass electrophoresis gel (ATTO e-PAGEL), and electrophoresis was performed (40 mA, 30 minutes). After removing the gel, the gel was stained with Coomassie brilliant blue (Bio-Rad Bio-safe CBB), followed by decoloring the gel with distilled water. FIG. 2 shows the result of SDS-PAGE of the enzyme liquid itself of Accellerase Duet, which is a commercially available cellulase. FIG. 3 shows the result of SDS-PAGE of the supernatant obtained after SDS treatment of the water-insoluble cellulase-treated product prepared by enzyme (Accellerase Duet) treatment of the explosion-treated biomass.

By such a method, a group having specific molecular weights characteristic to cellulase can be found, and this allows judgment of whether the filter aid was treated with enzyme or not. In FIGS. 2 and 3, each of the right lane in FIG. 2 and the left lane in FIG. 3 corresponds to the electrophoretic profile of a standard sample containing many stained proteins having known molecular weights. The peak between the molecular weights of 75 kDa and 100 kDa indicated by the standard samples corresponds to cellobiohydrolase. Therefore, it can be said that, among adsorbed enzymes, the amount of cellobiohydrolase is large based on comparison between FIGS. 2 and 3. That is, whether a product is our filter aid or not can be confirmed by subjecting the filter aid to the above treatment to see whether cellobiohydrolase is attached thereto.

Reference Example 10 Ratio of Solid Content Added

The hydrothermally treated liquid and the water-insoluble cellulase-treated product prepared by enzyme treatment of the hydrothermally treated biomass, or the yeast liquid and the water-insoluble cellulase-treated product prepared by enzyme treatment of the ammonia-treated cellulose, were used to study how much solids concentration is preferred. The solids concentration herein means the value obtained by measuring the water content of each filter aid and measuring the dry weight, followed by dividing the value by the total amount of the filter aid and the liquid to be treated. The turbidity observed after addition of each liquid and the filter press treatment is shown in Table 17 (the turbidity after each treatment [unit: NTU]). In the case where the solids concentration was 25%, no filtrate could be obtained since the slurry to be subjected to filter press treatment could be hardly transferred.

TABLE 17

| Solids concentration | 0.5% | 1.0% | 5.0% | 10% | 15% | 20% | 25% |
|---|---|---|---|---|---|---|---|
| Hydrothermally treated liquid | 120 | 5 | 3 | 3 | 4 | 8 | Failed to obtain filtrate |
| Yeast liquid | 50 | 3 | 2 | 2 | 3 | 5 | Failed to obtain filtrate |

Reference Example 11 Analysis of Composition of Biomass Before and after Enzyme Treatment By the method described in Reference Example 4, the composition ratios before and after the enzyme treatment in Example 3 (hydrothermal treatment) and Example 6 (ammonia treatment) were analyzed. The results are shown in Table 18 (the composition before and after the enzyme treatment of the hydrothermally treated biomass) and Table 19 (the composition before and after the enzyme treatment of the aqueous-ammonia-treated biomass), respectively. It can be seen that the degradation residue rate of the enzyme-treated product was not less than 1.5 times higher than that before the enzyme treatment. This is assumed to be due to a relative increase in the degradation residue rate caused by degradation of mainly the cellulose component.

TABLE 18

|  | Before enzyme treatment | After enzyme treatment |
|---|---|---|
| Xylose | 3.02% | 1.43% |
| Arabinose | 0.08% | 0.02% |
| Mannose | 0.16% | 0.19% |
| Glucose | 56.7% | 33.1% |
| Galactose | 0.26% | 0.12% |
| Degradation residue rate | 33.4% | 59.3% |
| Total | 93.5% | 94.2% |

TABLE 19

|  | Before enzyme treatment | After enzyme treatment |
|---|---|---|
| Xylose | 22.26% | 13.25% |
| Arabinose | 3.15% | 1.41% |
| Mannose | 0.36% | 0.39% |
| Glucose | 40.9% | 45.0% |
| Galactose | 0.95% | 0.80% |
| Degradation residue rate | 17.3% | 30.9% |
| Total | 84.9% | 91.8% |

Reference Example 12 Change in Particle Size

Figure 4:
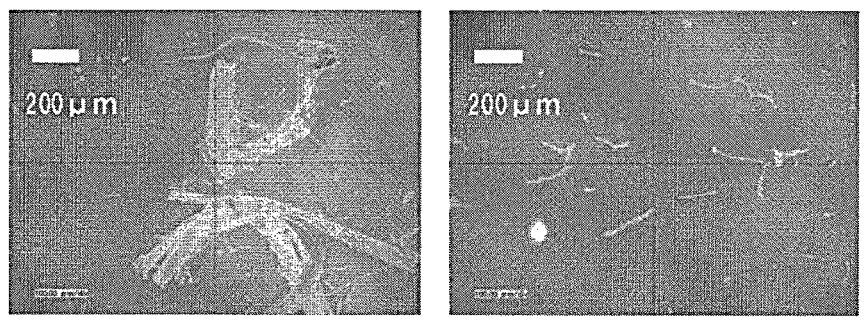
FIG. 4 shows optical micrographs showing the conditions of a hydrothermally treated product, which micrographs were taken before and after enzyme treatment.
Figure 5:
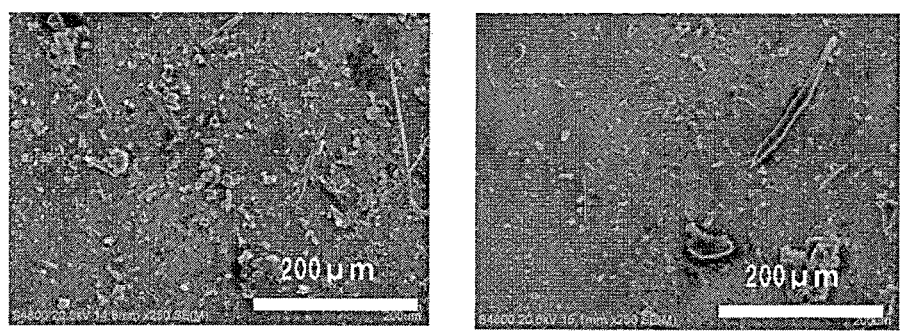
FIG. 5 shows SEM images showing the conditions of an aqueous-ammonia-treated product, which images were taken before and after enzyme treatment.

FIGS. 4 and 5 show micrographs showing the states of the product before and after the enzyme treatment in Example 3 (hydrothermal treatment), and SEM images showing the states of the product on the microfiltration membrane before and after the enzyme treatment in Example 6 (ammonia treatment), respectively. It can be seen from FIG. 4 and FIG. 5 that the sizes were decreased by the enzyme treatment. The treated product in FIG. 4 contained a large amount of particles having sizes of about 200 μm. Therefore, as in Comparative Example 8 and JP 9-173728 A, it is assumed that the filter aid has a mechanism other than reduction in the particle size, which mechanism allows removal of suspended materials.

The invention claimed is:

1. A filtration method comprising filtering a high turbidity liquid containing a lignin component together with a filter aid obtained by the method of producing a filter aid comprising:

(A) obtaining a pretreated biomass by thermochemical treatment, which is at least one selected from the group consisting of acid treatment, alkali treatment, ammonia treatment, steam explosion treatment and hydrothermal treatment, of a cellulose-containing biomass;

(B) treating said pretreated biomass obtained in (A) with cellulase to obtain a cellulase-treated product; and (C) obtaining a solid content of said cellulase-treated product of (B), wherein said cellulose-containing biomass is a herbaceous biomass, wherein the turbidity of said high turbidity liquid is not less than 1000 NTU.

2. The method according to claim 1, wherein said filtering is conducted by filter press.

3. The filtration method according to claim 1, wherein an amount of dry product of said filter aid is not less than 0.5% by mass and less than 25% by mass with respect to the liquid to be filtered.

* * * * *